United States Patent
Liu et al.

(10) Patent No.: US 8,969,832 B2
(45) Date of Patent: Mar. 3, 2015

(54) ELECTROTHERMAL VAPORIZATION ATOMIC FLUORESCENCE SPECTROSCOPY AND SPECTROMETER FOR DETERMINATION OF CADMIUM

(75) Inventors: Jixin Liu, Beijing (CN); Li Feng, Beijing (CN); Dong Lu, Beijing (CN); Fengxi Zheng, Beijing (CN); Junwei Li, Beijing (CN)

(73) Assignee: Beijing Titan Instruments Co., Ltd., Beijing (CN)

( * ) Notice: Subject to any disclaimer, the term of this patent is extended or adjusted under 35 U.S.C. 154(b) by 0 days.

(21) Appl. No.: 13/810,147

(22) PCT Filed: Jul. 15, 2010

(86) PCT No.: PCT/CN2010/075178
§ 371 (c)(1),
(2), (4) Date: Jan. 14, 2013

(87) PCT Pub. No.: WO2012/006782
PCT Pub. Date: Jan. 19, 2012

(65) Prior Publication Data
US 2013/0119271 A1 May 16, 2013

(51) Int. Cl.
*F21V 9/16* (2006.01)
*G01J 3/44* (2006.01)
*G01N 21/64* (2006.01)
*G01N 1/40* (2006.01)

(52) U.S. Cl.
CPC ....... *G01J 3/4406* (2013.01); *G01N 2021/6417* (2013.01); *G01N 2001/4033* (2013.01); *G01N 1/4022* (2013.01); *G01N 21/6402* (2013.01)
USPC ..................................... 250/458.1

(58) Field of Classification Search
USPC ....................................... 250/458.1
See application file for complete search history.

(56) References Cited

U.S. PATENT DOCUMENTS

| 4,833,322 A | * | 5/1989 | Forster et al. | 250/288 |
| 5,191,212 A | * | 3/1993 | Falk et al. | 250/288 |
| 5,316,955 A | * | 5/1994 | Govorchin | 436/155 |

(Continued)

OTHER PUBLICATIONS

Authors: Xiaodong Wen, Peng Wu, Li Chen, Xiandeng Hou, Title: Determination of cadmium in rice and water by tungsten coil electrothermal vaporization-atomic fluorescence spectrometry and tungsten coil electrothermal atomic absorption spectrometry after cloud point extraction, Date: Feb. 4, 2009, Publisher: Analytica Chimica Acta 650 (2009) 33-38.*

(Continued)

*Primary Examiner* — Kiho Kim
*Assistant Examiner* — Taeho Jo

(57) ABSTRACT

An electrothermal vaporization atomic fluorescence spectrometer for determination of Cadmium comprising a sampling system, a light source, an atomizer, a light path system, a detection system, and a display device. The sampling system includes an electrothermal vaporization device and a capture trap; the capture trap comprises a Tungsten or Molybdenum coil (6), a holder (15), a cover (7) and a power supply (17); the cover (7) and the holder (15) form a sealed space; the Tungsten or Molybdenum coil (6) is arranged on the holder (15); the Tungsten or Molybdenum coil (6) is located inside the sealed space formed by the cover (7) and the holder (15); and the cover (7) is provided with an inlet (12) and an outlet (13) thereon. An electrothermal vaporization atomic fluorescence spectroscopy for determination of Cadmium is also provided.

6 Claims, 1 Drawing Sheet

(56) References Cited

U.S. PATENT DOCUMENTS

| | | | |
|---|---|---|---|
| 5,705,787 A * | 1/1998 | Karanassios | 219/121.52 |
| 2004/0056044 A1* | 3/2004 | Hirahara et al. | 222/3 |
| 2004/0056368 A1* | 3/2004 | Hirahara et al. | 261/64.3 |
| 2005/0195393 A1* | 9/2005 | Karanassios | 356/316 |

OTHER PUBLICATIONS

Authors: Peng Wu a, Xiaodong Wen b, Liang Heb, Yihua Heb, Minzh, Title: Evaluation of tungsten coil electrothermal vaporization-Ar/H2 flame atomic fluorescence spectrometry for determination of eight traditional hydride-forming elements and cadmium without chemical vapor generation, Date: Jun. 19, 2007, Publisher: ScienceDirect.*

Authors: Li Feng and Jixin Liu, Title: Solid sampling graphite fibre felt electrothermal atomic fluorescence spectrometry with tungsten coil atomic trap for the determination of cadmium in food samples, Date: Apr. 23, 2010, Publisher: Journal of Analytical Atomic Spectrometry.*

Authors: Xiandeng Hou, Bradley T. Jones, Title: Field instrumentation in atomic spectroscopy, Date:2000, Publisher: Microchemical Journal 66(2000) 115-145.*

* cited by examiner

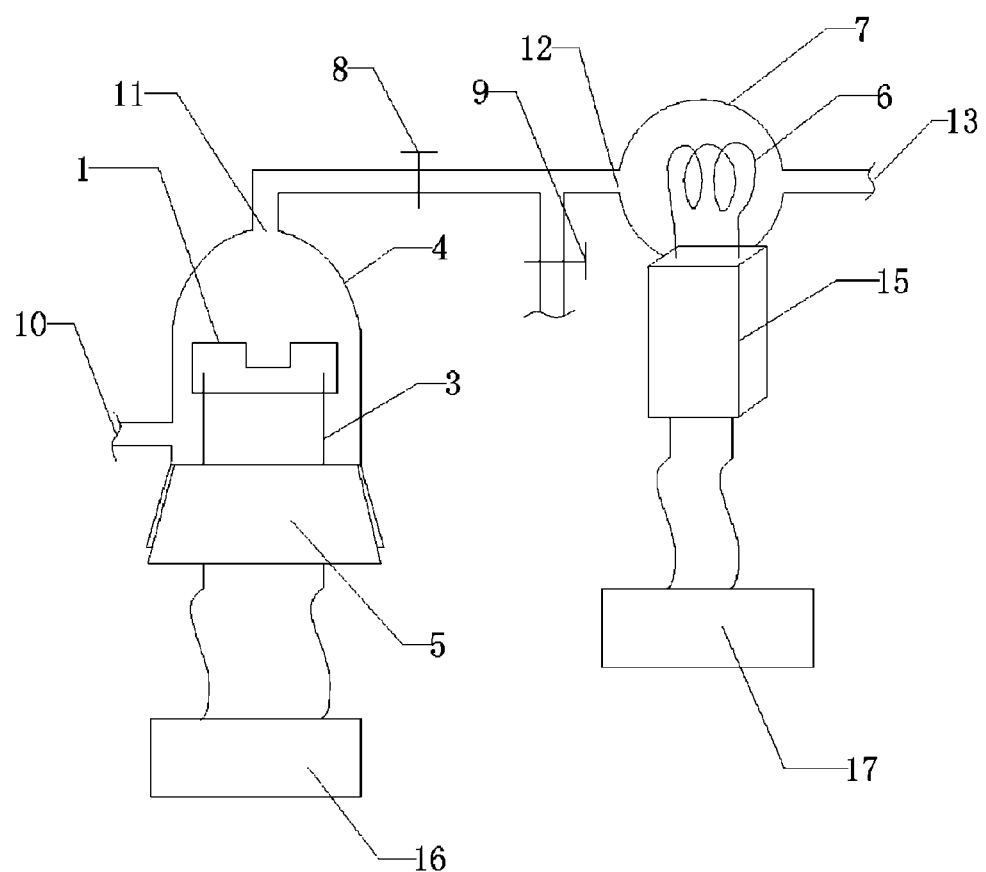

ELECTROTHERMAL VAPORIZATION ATOMIC FLUORESCENCE SPECTROSCOPY AND SPECTROMETER FOR DETERMINATION OF CADMIUM

CROSS REFERENCE OF RELATED APPLICATION

This is a U.S. National Stage under 35 U.S.C 371 of the International Application PCT/CN2010/075178, filed Jul. 15, 2010.

BACKGROUND OF THE PRESENT INVENTION

1. Field of Invention

The present invention relates to an electrothermal vaporization atomic fluorescence spectroscopy and spectrometer for determination of Cadmium.

2. Description of Related Arts

Owing to the sewage irrigation in large quantities and abuse of fertilizer, China suffers severe Cadmium (Cd) pollution, with some areas having reached the point of producing "Cadmium rice". For example, in a sewage-irrigated local site of city Shenyang, the Cd concentration in the locally-produced rice was as high as 0.4-1.0 mg/kg, which have reached or exceeded the average "bone pain illness"-inducing Cd concentration. In view of this, the technology for quick determination of Cd has in recent years attracted wide attention, and has developed a series of quick measuring methods based on biosensors, colorimetry, enzyme inhibition, electrochemistry and atomic spectrum, etc. However, most of these methods can only determine the heavy metal ions in solution, and still can't avoid the time-consuming and laborious sample pre-treatment process; and as a result of matrix interference it is difficult to achieve accurate measurement, leading to high false-reporting rates. Although it can be achieved in great degree to simplify the heavy metal measurement for soil and agricultural products, it can't completely solve this difficult problem. The way to really realize direct determination of heavy metals in soil and agricultural products is nevertheless the atomic spectral methods which use Electrothermal Vaporization (ETV) or Laser Ablation (LA) as the means of sample introduction. Among the atomic spectral methods, the relatively mature techniques of Electrothermal Vaporization-Inductively Coupled Plasma Optical Emission Spectrometry (ETV-ICPOES), Mass Spectrometry (ETV-ICPMS) or Graphite Furnace Atomic Absorption Spectroscopy (GFAAS) have all been reported in use for the measurement by direct sampling. With the development in background correction technology and continuous light source technology, the direct sampling technique using electrothermal vaporization is more and more approaching real application. However, for the application in the field of quick determination for soil and agricultural products, although the above-mentioned technologies can inhibit the matrix interference to a certain degree, it is still difficult to fully overcome the problem, and it remains an unsolved problem for more complex matrices. Therefore, when using electrothermal evaporation as the means of sample introduction, the above-mentioned detection problem is practically to develop a method to eliminate the matrix interference, so as to meet a variety of complex matrices.

Atomic Fluorescence Spectroscopy (AFS) is a relatively rapidly developed atomic spectroscopy technique in China, which can use dispersion-free measurement thanks to its simple spectra and less spectra overlapping of atomic fluorescence. This greatly simplifies the instrument structure, makes it easy to realize miniaturization, and gives the possibility to be used in field measurement. But the currently commonly-used atomic fluorescence spectrometers use the Hydride Generation (HG)-based sample introduction technique. What have been reported in the literature about the electrothermal vaporization atomic fluorescence spectrometer include the measurement of Lead in solution by using graphite furnace as the evaporation and atomization device, and the measurement of heavy metals in solution after being digested by using Tungsten Coil (TC)-based Electrothermal Evaporation-Atomic Fluorescence Spectroscopy (ETV-AFS). Although these two types of device mentioned above possesses the potential of direct sampling by using ETV, it is still difficult to completely solve the matrix interference problem.

Matrix interference has been a major problem puzzling the atomic spectroscopy using direct sampling. Although the problem can be alleviated after matrix correction, it can't fundamentally solve the problem, and it is necessary to figure out a way otherwise. The development of the solid Mercury measurement technique based on atomic absorption since the 90s of last century provides a good inspiration. This technique carries out the measurement as follows: first release the Mercury in atomic form while decomposing the organic matter by oxidation through sample combustion in pure oxygen or air and further catalytic combustion; then separate the atomic Mercury from the matrix after being captured by Gold-bearing adsorption agent; and finally reheat the adsorbent to release the captured Mercury and introduce it into the atomic absorption spectrometer by carrier gas for measurement. This technique realizes the separation of Mercury from its matrix by using a highly selective noble metal capture trap, thereby completely eliminating the matrix interference. This shows that the on-line trapping technique should be a very efficient means for eliminating matrix interference. When used for Cd measurement, as currently reported in the literature, the on-line trapping technique can in most cases only capture hydrides or free atoms formed in the flame, while the capture of Cd introduced by electrothermal vaporization has not yet been reported. This is mainly due to the reason that, under normal conditions, the Cd formed by electrothermal vaporization exists mostly in the form of nanoparticles, which can't be efficiently trapped.

SUMMARY OF THE PRESENT INVENTION

The objective of the present invention is to provide an electrothermal vaporization atomic fluorescence spectroscopy and spectrometer for determination of Cadmium, which can efficiently eliminate matrix interference.

The electrothermal vaporization atomic fluorescence spectrometer for determination of Cadmium provided in the present invention comprises a sampling system, a light source, an atomizer, a light path system, a detection system, and a display device, wherein: the sampling system includes an electrothermal vaporization device and a capture trap; the capture trap consists of a Tungsten or Molybdenum coil, a holder, a cover and a power supply; the cover and the holder form a sealed space; the Tungsten or Molybdenum coil is arranged on the holder; the Tungsten or Molybdenum coil is located inside the sealed space formed by the cover and the holder; and the cover is provided with an inlet and an outlet thereon.

In the electrothermal vaporization atomic fluorescence spectrometer for determination of Cadmium in the present invention: the electrothermal vaporization device comprises a shielding cover, an evaporation boat, electrodes, an electrode holder and a power supply; the electrodes are located under the evaporation boat, and connected to the evaporation boat; the electrodes are disposed on the electrode holder, and electrically connected to the power supply; the shielding cover and the electrode holder form a sealed space, and the evaporation boat is located inside the sealed space; the shielding cover and the electrode holder are movably connected; the shielding cover is provided with an inlet and an outlet thereon; and the outlet of the shielding cover is connected to the inlet of the cover of the capture trap via a three-way pipe.

In the electrothermal vaporization atomic fluorescence spectrometer for determination of Cadmium in the present invention: the three-way pipe is provided with a first switching valve for its main pipeline, and a second switching valve for its branch pipeline.

The electrothermal vaporization atomic fluorescence spectroscopy for determination of Cadmium provided in the present invention consists of the following steps:

dry a sample to be measured in the air, ash it, and collect the ash;

under an Argon gas atmosphere, increase the ash temperature to 1600~2000° C., and make a resulting steam contact a Tungsten or Molybdenum coil; and under an Hydrogen and Argon gas atmosphere, increase the temperature of the Tungsten or Molybdenum coil to 1600~2000° C., release Cadmium atom, and measure the Cadmium content by analysis of the fluorescence spectroscopy.

In the electrothermal vaporization atomic fluorescence spectroscopy for determination of Cadmium in the present invention: under the Hydrogen and Argon gas atmosphere, the volume percentage of the Hydrogen gas is 10~90%.

BRIEF DESCRIPTION OF THE DRAWINGS

FIG. 1 is the structure diagram of the sampling system of the electrothermal vaporization atomic fluorescence spectrometer for determination of Cadmium in the present invention.

DETAILED DESCRIPTION OF THE PREFERRED EMBODIMENT

The electrothermal vaporization atomic fluorescence spectrometer for determination of Cadmium in the present invention comprises a sampling system, a light source, an atomizer, a light path system, a detection system, and a display device, wherein: the light source, atomizer, light path system, detection system and display device are identical with those in the existing fluorescent spectrometer; and the connection and position relationship between the light source, light path system, detection system, display device, and atomizer is identical with that in the existing atomic fluorescence spectrometer. The only difference from the existing technique is in the structure of sampling system. The sampling system in the present invention includes an electrothermal vaporization device and a capture trap. The electrothermal vaporization device in the present invention comprises a shielding cover 4, an evaporation boat 1, an electrodes 3, an electrode holder 5 and a power supply 16, wherein: the electrodes 3 are located under the evaporation boat 1, and connected to the evaporation boat 1; the electrode holder 5 supports the electrodes 3; the power supply 16 and the electrodes 3 are electrically connected; the shielding cover 4 and the electrode holder 5 are joined by fastening, and form a sealed space; the evaporation boat 1 is located inside the sealed space; the shielding cover 4 and the electrode holder 5 are movably connected; when opening the shielding cover 4, the evaporation boat 1 is exposed to the air; the shielding cover 4 is provided with an inlet 10 and an outlet 11 thereon. The capture trap in the present invention comprises a Tungsten or Molybdenum coil 6, a holder 15, a cover 7 and a power supply 17, wherein: the cover 7 and the holder 15 are joined by fastening, and form a sealed space; the holder 15 supports the Tungsten or Molybdenum coil 6; the Tungsten or Molybdenum coil 6 is located inside the sealed space formed by the cover 7 and the holder 15; the cover 7 is provided with an inlet 12 and an outlet 13 thereon; the outlet 11 of the shielding cover 4 is connected to the inlet 12 of the cover 7 via a three-way pipe, where a first switching valve 8 is provided for its main pipeline, and a second switching valve 9 is provided for its branch pipeline.

Place the sample in the evaporation boat 1 of the atomic fluorescence spectrometer for determination of Cadmium in the present invention. Open the shielding cover 4, and expose the evaporation boat 1 to the air. Heat the evaporation boat 1 to increase the temperature of the evaporation boat 1 to 450~600° C. Dry the sample, and ash it. Then, close the shielding cover 4, and form a sealed space by the shielding cover 4 and the electrode holder 5. Introduce the Argon gas from the inlet 10 of the shielding cover 4. Open the first switching valve 8, and close the second switching valve 9. Increase the temperature of the evaporation boat 1 to 2000° C., release the Cd in the sample as free Cd atom, and introduce it into the capture trap. Capture the free Cd atom by highly selective Tungsten or Molybdenum coil 6. Then, close the first switching valve 8, and open the second switching valve 9. Introduce the gas mixture of Hydrogen (10%~90%) and Argon (10%~90%) via the branch pipeline. Increase the temperature of the Tungsten or Molybdenum coil 6 to 1600~2000° C., and release the Cd atom again. Excite the free Cd atom by the hollow cathode lamp which surrounds the atomizer, and emit fluorescence signal. Focus the signal using lens, and detect it by the detection system through the light path system.

Take 10 mg cabbage (a GB standard substance under the GBW10014) as an example. Measure the Cadmium content in the sample using the atomic fluorescence spectrometer for determination of Cadmium in the present invention, and get the result of 41 microgram/kg, which falls within the range of standard value of 35±6 microgram/kg for this standard sample. For standard samples at high, middle and low levels (20, 40, 80 microgram/kg), the recovery rates all fall within the range of 90~110%.

Take the 10 mg rice flour (a GB standard substance under the GBW (E) 080684) as an example. Measure the Cadmium content in the sample using the atomic fluorescence spectrometer for determination of Cadmium in the present invention, and get the result of 7.8 microgram/kg, which falls within the range of standard value of 9±4 microgram/kg for this standard sample. For standard samples at high, middle and low levels (20, 40, 80 microgram/kg), the recovery rates all fall within the range of 90~105%.

The two examples described above shows that this method can accurately measure the Cd content in solid samples.

The above embodiments merely serve to describe the preferred embodiments of the present invention, and do not put any restrictions on the scope of the present invention. Under the premise of the present invention and without departing from the spirit of the present invention design, the various modifications and improvements on the technical solution of the present invention made by the ordinary engineering and technical personnel in this field of art should all fall into the scope of protection stipulated in the Claims of the present invention.

INDUSTRIAL APPLICATION

The electrothermal vaporization atomic fluorescence spectroscopy and spectrometer for determination of Cadmium in the present invention can highly selectively capture the free Cadmium atom by using free Cadmium atom capture trap, and then release the captured Cadmium again under the reducing atmosphere. Thus it can efficiently eliminate the matrix interference and realize the accurate measurement of Cadmium.

What is claimed is:

1. An electrothermal vaporization atomic fluorescence spectrometer for determination of Cadmium comprising a sampling system, a light source, an atomizer, a light path system, a detection system, and a display device, wherein the sampling system comprises an electrothermal vaporization device, for releasing Cd in a sample as free Cd atom, and a capture trap, for selectively capturing the free Cd atom, and releasing the captured free Cd atom again; wherein:

the electrothermal vaporization device comprises a shielding cover, an evaporation boat for containing the sample, electrodes, an electrode holder and a power supply; the electrodes is located under the evaporation boat, and connected to the evaporation boat; the electrodes are arranged on the electrode holder; the power supply and electrodes are electrically connected; the shielding cover and the electrode holder form a sealed space; the evaporation boat is located inside the sealed space; the shielding cover and the electrode holder are movably connected, in such a manner that, by opening the shielding cover, the evaporation boat is exposed to air, and by closing the shielding cover, the sealed space between the shielding cover and the evaporation boat is formed; the shielding cover is provided with inlet and outlet thereon; when the evaporation boat is exposed to the air, the evaporation boat is heated to 450~600° C. to heat, dry and ash the sample; then, when the sealed space between the shielding cover and the evaporation boat is formed, the evaporation boat is heated to 2000° C. to release the Cd in the sample as the free Cd atom;

the capture trap comprises a Tungsten or Molybdenum coil for selectively capturing the free Cd atom at a temperature lower than 1600° C., and releasing the captured free Cd atom again at 1600~2000° C., a holder, a cover and a power supply; the cover and the holder form a sealed space; the Tungsten or Molybdenum coil is arranged on the holder; the Tungsten or Molybdenum coil is located inside the sealed space formed by the cover and the holder; and the cover is provided with an inlet and an outlet thereon; and the outlet of the shielding cover is connected to the inlet of the cover of the capture trap via a three-way pipe, for introducing the free Cd atom from the electrothermal vaporization device into the capture trap; and wherein the free Cd atom released again is introduced from the capture trap into the light source which surrounds the atomizer to be excited, then detected by the detection system through the light path system.

2. The electrothermal vaporization atomic fluorescence spectrometer for determination of Cadmium according to claim 1, wherein the three-way pipe is provided with a first switching valve for its main pipeline, and a second switching valve for its branch pipeline.

3. The electrothermal vaporization atomic fluorescence spectrometer for determination of Cadmium according to claim 2 wherein the Tungsten or the Molybdenum coil selectively captures the free Cd atom at a temperature ranging from a room temperature to 250° C.

4. An electrothermal vaporization atomic fluorescence spectroscopy for determination of Cadmium, comprising the following steps:

drying a sample to be measured in the air, ashing it, and collecting the ash;

under an Argon gas atmosphere, increasing the ash temperature to 1600~2000° C. to generate a resulting vapor, so as to release Cadmium atom in the sample as free Cd atom for a first time:

making the resulting vapor contact a Tungsten or Molybdenum coil at a temperature lower than 1600° C. to selectively capture the Cadmium atom therein; and under an Hydrogen and Argon gas atmosphere, increasing the temperature of the Tungsten or Molybdenum coil to 1600~2000° C. to release the captured Cadmium atom again, and measuring the Cadmium content by analysis of the atomic fluorescence spectroscopy.

5. The electrothermal vaporization atomic fluorescence spectroscopy according to claim 4, wherein under the Hydrogen and Argon gas atmosphere, the volume percentage of the Hydrogen gas is 10~90%.

6. The electrothermal vaporization atomic fluorescence spectroscopy according to claim 5, wherein the step of "making the resulting vapor contact a Tungsten or Molybdenum coil at a temperature lower than 1600° C. to selectively capture Cadmium atom therein" comprises: making the resulting vapor contact a Tungsten or Molybdenum coil at a temperature ranging from a room temperature to 250° C. to selectively capture Cadmium atom therein.

* * * * *